United States Patent [19]
Guittard et al.

[11] Patent Number: 5,698,224
[45] Date of Patent: Dec. 16, 1997

[54] TACRINE THERAPY

[75] Inventors: George V. Guittard, Cupertino; Jerry D. Childers, Menlo Park; Patrick S. -L. Wong, Palo Alto; Fernando E. Gumucio, Santa Clara; David J. Kidney, Sunnyvale, all of Calif.

[73] Assignee: Alza Corporation, Palo Alto, Calif.

[21] Appl. No.: 266,045

[22] Filed: Jun. 27, 1994

[51] Int. Cl.$^6$ .............................. A61K 9/00; A61K 31/13; A61K 31/135
[52] U.S. Cl. .................. 424/468; 424/471; 424/472; 424/480; 514/297
[58] Field of Search ........................ 424/439, 451, 424/452, 457, 463, 486, 488, 468, 471, 472, 480

[56] References Cited

U.S. PATENT DOCUMENTS

| | | | |
|---|---|---|---|
| 2,799,241 | 7/1957 | Wuster | 118/24 |
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,327,725 | 5/1982 | Cortese et al. | 128/260 |
| 4,612,008 | 9/1986 | Wong et al. | 604/892 |
| 4,765,989 | 8/1988 | Wong et al. | 424/473 |
| 4,783,337 | 11/1988 | Wong et al. | 424/468 |
| 4,816,456 | 3/1989 | Summers | 514/255 |
| 4,857,330 | 8/1989 | Stephen et al. | 424/424 |

FOREIGN PATENT DOCUMENTS

| | | |
|---|---|---|
| A0595365 | 5/1994 | European Pat. Off. . |
| WOA9215285 | 9/1992 | WIPO . |
| WOA9324154 | 12/1993 | WIPO . |
| WOA9503052 | 2/1995 | WIPO . |

OTHER PUBLICATIONS

Preparation of Compressed TAblet Granulations by the Air–Suspension Technique II*, Wurster, Dale E., Sci. Ed., vol. 49, (1960).

Air–Suspension Techniqur of Coating Drug Particles*, Wurster, Dale E. J. AM. PHAR. ASSOC., Sci. Ed., vol. 48 (1959).

*Primary Examiner*—Jeffrey C. Mullis
*Attorney, Agent, or Firm*—Paul L. Sabatine; Steven F. Stone; Michael J. Rafa

[57] ABSTRACT

A dosage form is disclosed for administering 10 ng to 1200 mg tacrine to a patient in need of tacrine therapy.

2 Claims, 2 Drawing Sheets

TACRINE THERAPY

FIELD OF THE INVENTION

This invention pertains to tacrine therapy indicated for the management of Alzheimer's disease. More particularly, the invention relates to a dosage form that provides a controlled delivery of tacrine over an extended time for the treatment of Alzheimer's disease. The invention concerns additionally a therapeutic composition of matter comprising tacrine useful for treating Alzheimer's disease. The invention relates further to a method of administering tacrine to produce a beneficial effect for treating Alzheimer's disease.

BACKGROUND OF THE INVENTION

The drug tacrine is indicated for the treatment of Alzheimer's disease. Alzheimer's disease is a progressive irreversible brain disorder that strikes more frequently with advancing age. The common symptoms of the disease generally include memory loss, confusion, impaired judgment, personality changes, and the loss of language skills. There is, during the course of the disease a dependence on others to assist the patient in performing tasks such as taking medicine. The average length of the illness is seven years but it can last fifteen or more years. Presently, research indicates the symptoms of Alzheimer's disease are the result of the loss of nerve cell function in distinct areas of the brain. Alzheimer's disease affects an estimated four million people, and most cases occur after age sixty; however, the disease affects some individuals in their forties and fifties, usually affecting about ten percent of people over sixty-five. Alzheimer's disease affects all people, and the disease is not restricted to any race, gender, or socioeconomic class.

The drug tacrine for treating Alzheimer's disease is disclosed in U.S. Pat. No. 4,816,456 issued to patentee Summers. The patent teaches the drug tacrine can be administered by standard noncontrolled tablet, pill, powder, elixir, solution, suppository, ointment, cream and capsule that are dose-dumping conventional forms. The conventional forms deliver the drug by dumping and this leads to uneven dosing of drug, to uneven blood levels of the drug characterized by peaks and valleys, and accordingly this does not provide controlled-rate therapy over an extended period of time. Presently, tacrine is administered many times a day because tacrine has a half-life of about three hours. The prior art dosing patterns and the half-life characteristics of tacrine dictate of the need for an unique dosage form that can administer tacrine at a controlled rate over an extended therapeutic time to provide continuous therapy and beneficial therapy to an Alzheimer patient. The medical history of Alzheimer's disease is known in *Current Therapy*, by Conn, pgs 831–835 (1994).

The prior art provided dosage forms that can administer many drugs for continuous-controlled therapy. For example, in U.S. Pat. Nos. 3,845,770 and 3,916,899 issued to Theeuwes and Higuchi, in U.S. Pat. No. 4,327,725 issued to Cortese and Theeuwes, and in U.S. Pat. Nos. 4,612,008; 4,765,989; and 4,783,337 issued to Wong, Barclay, Deters and Theeuwes a dosage form is disclosed that provides therapy by an osmotic pressure generated inside the dosage form. The dosage form of these patents operates successfully for delivering a drug that develops a high osmotic pressure gradient across a semipermeable membrane. The drug tacrine, however, possesses a low osmotic pressure, which dictates against providing an osmotic dosage form for use in the gastrointestinal tract. The gastrointestinal tract is a high osmotic pressure environment, and this speaks against an osmotic dosage form comprising tacrine as it can adversely affect the desired delivery of tacrine from the dosage form in this environment.

It is apparent immediately in the light of the above presentation, that an urgent need exists for a dosage form endowed with the necessary physical-chemical properties for delivering tacrine. The need exists for a dosage form for delivering tacrine at a rate-controlled in a continuous dose in a therapeutic tacrine range governed by the dosage form while, simultaneously providing the beneficial tacrine therapy. It will be appreciated by those versed in the drug dispensing art, that if such a dosage form is provided that can administer tacrine in the desired delivery program, the dosage form comprising tacrine would represent an advancement and valuable contribution in Alzheimer therapy.

OBJECTS OF THE INVENTION

Accordingly, in view of the above presentation, it is an immediate object of this invention to provide a dosage form that delivers tacrine for the management of Alzheimer's disease.

Another object of the present invention is to provide a dosage form for administering tacrine at a controlled-rate in a continuous-therapeutic dose over an extended period of time.

Another object of the invention is to provide tacrine in a rate-controlled-continuous-release dose to an Alzheimer patient for maintaining an substantially constant tacrine level in the blood as a function of the prolonged-release system.

Another object of the present invention is to provide a dosage form that can deliver tacrine in the gastrointestinal environment and concomitantly substantially reduces and/or substantially eliminates the unwanted influence of the gastrointestinal environment of the delivery of tacrine in the gastrointestinal tract.

Another object of the present invention is to provide an improvement in a dosage form that administers tacrine; wherein the improvement comprises delivering tacrine in a continuous-release dose from the dosage form for predictable and improved therapy orally to a patient in need of tacrine therapy.

Another object of the invention is to provide a method for administering tacrine by orally administering tacrine in a known dose per unit time over an extended time to a patient in need of tacrine therapy while simultaneously substantially avoiding a toxic range of tacrine.

Another object of the present invention is to provide a therapeutic composition comprising tacrine blended with a tacrine pharmaceutically acceptable compatible carrier.

Another object of the invention is to provide a dosage form that delivers tacrine and is characterized as clinically practical by reducing tacrine dosing frequency, reducing fluctuation in circulating tacrine levels and increases patient compliance to provide a more uniform tacrine pharmacological response.

Another object of the present invention is to provide a therapeutic composition comprising tacrine and pharmaceutically acceptable polymers comprised into a dosage form.

Other objects, features and advantages of the invention will be more apparent to those versed in the dispensing art from the accompanying detailed specification, taken in conjunction with the accompanying drawing figures and claims.

BRIEF DESCRIPTION OF THE DRAWINGS

In the drawing figures, which are not drawn to scale, but are set forth to illustrate various embodiments of the invention, the drawing figures are as follows.

Drawing

Drawing

Drawing

Drawing

Drawing

Drawing

In the drawing and in the specification, like parts in related figures are identified by like numbers. The terms appearing earlier in the specification, and in the description of the drawings, as well as embodiments thereof are further described in this specification.

DETAILED DESCRIPTION OF THE DRAWINGS

Figure 1:
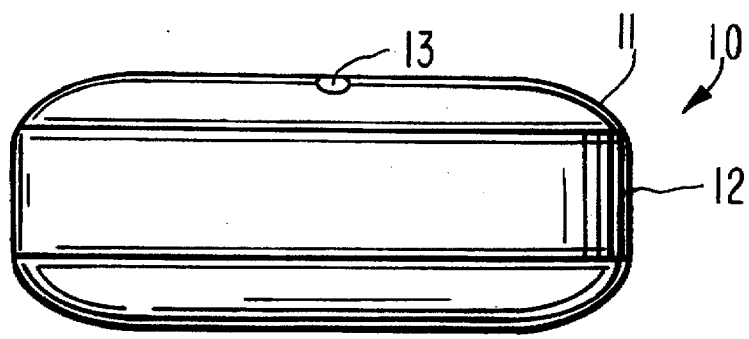
FIG. 1 is a general view of a dosage form designed and shaped for the oral administration of tacrine at a rate-controlled tacrine to a patient in need of tacrine therapy.

Turning now to the drawing figures in detail, which drawing figures are examples of dosage forms provided by this invention, and which examples are not to be construed as limiting, one example of a dosage form is seen in drawing FIG. 1. In drawing FIG. 1, a dosage form 10 is seen comprising a body member 11, which body member 11 comprises a wall 12 that surrounds and forms an internal area, not seen in drawing FIG. 1. Drawing FIG. 10 comprises at least one exit 13 that connects the exterior of dosage form 10 with the interior of dosage form 10. The dosage form 10 of drawing FIG. 1 illustrates a controlled-release dosage form that delivers tacrine over an extended time. The dosage form comprising controlled-release properties provided by this invention is successful at maintaining substantially therapeutic tacrine levels in the blood or in body tissues. The dosage form provided by the invention comprises continuous-extended release of tacrine over a prolonged time. The dosage form provides tacrine blood levels and tissue levels within a therapeutic range optionally below side-effect levels over time. An extended period of time, as used for the purpose of this invention includes a prolonged period up to thirty hours, over that achieved by conventional drug delivery forms such as conventional nonrate, immediate release tablets and capsules.

Figure 2:
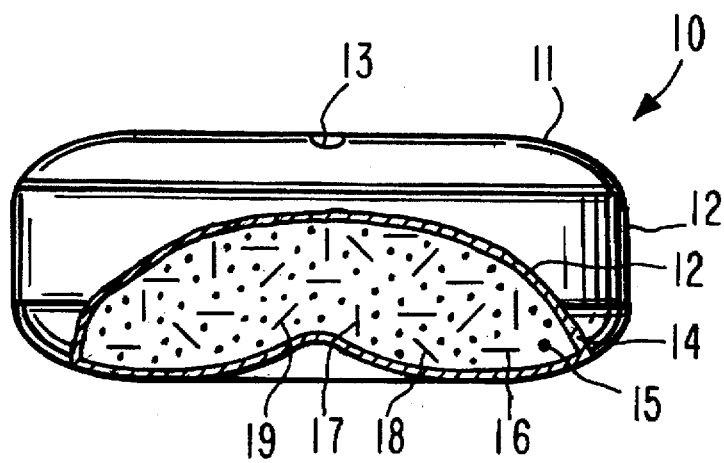
FIG. 2 is an opened view of drawing FIG. 1 depicting the dosage form comprising a pharmaceutical composition comprising tacrine and means for aiding in the delivery of tacrine from the dosage form.

In drawing FIG. 2, dosage form 10 is seen in opened section. In drawing FIG. 2, dosage form 10 comprises a body 11, a wall 12 that surrounds an internal area or compartment 14. Internal compartment 14 communicates through exit port 13 with the exterior of dosage form 10. Wall 12 of dosage form 10 comprises totally, or in part, is a composition that is permeable to the passage of an exterior fluid, such as an aqueous fluid or a biological fluid present in the gastrointestinal tract. Wall 12 is nontoxic and it is substantially inert, it maintains its physical and chemical integrity during the dispensing time of tacrine. The phrase, maintains its physical and chemical integrity means wall 12 does not lose its structure and it does not undergo chemical change during the dispensing of tacrine.

Wall 12, as used for all the dosage forms of this invention, comprises a composition that does not adversely effect an animal, a human, or the components of the dosage form. Compositions for forming wall 12 comprise a member selected from the group consisting of a cellulose ester polymer, a cellulose ether polymer, and a cellulose ester-ether polymer. These cellulosic polymers have a degree of substitution, D.S., on the anhydroglucose unit of the cellulose, from greater than 0 up to 3 inclusive. By degree of substitution is meant the average number of hydroxyl groups originally present on the anhydroglucose unit comprising the cellulose polymer that are replaced by a substituting group. Representative of wall-providing polymers comprises a member selected from the group consisting of cellulose acylate, cellulose diacylate, cellulose triacylate, cellulose acetate, cellulose diacetate, cellulose triacetate, mono- di- and tricellulose alkanylates, mono-, di-, and tricellulose alkenylates, mono-, di-, and tricellulose alkinylates, mono-, di-, and tricellulose aroylates. Exemplary polymers include cellulose acetate having a D.S. up to 1 and an acetyl content up to 21%; cellulose acetate having a D.S. of 1 to 2 and an acetyl content of 21 to 35%; cellulose acetate having a D.S. of 2 to 3 and an acetyl content of 35 to 44.8%. More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7; cellulose tricylates having a D.S. of 2.9 to 3 such as cellulose trivalerate; cellulose trilaurate; cellulose tripalmitate; cellulose trisuccinate; and cellulose trioctanoate; cellulose diacylates having a D.S. of 2.2. to 2.6 such as cellulose disuccinate, cellulose dipalmitate, cellulose dioctanoate, and cellulose dipentanoate; and co-esters of cellulose such as cellulose acetate butyrate and cellulose acetate propionate.

Additional semipermeable polymers comprise acetaldehyde dimethyl cellulose acetate; cellulose acetate ethyl carbamate; cellulose acetate methyl carbamate; cellulose acetate diethyl aminoacetate; semipermeable polyamides; semipermeable polyurethanes; semipermeable sulfonated polystyrenes; semipermeable cross-linked selective polymers formed by the coprecipitation of a polyanion and polycation as disclosed in U.S. Pat. Nos. 3,173,876; 3,276, 586; 3,541,005, 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); semipermeable cross-linked poly (vinylbenzyltrimethyl ammonium chloride); semipermeable polymers exhibiting a fluid permeability of $2.5 \times 10^{-8}$ to $2.5 \times 10^{-4}$ ($cm^2/hr.atm$) expressed per atmosphere of hydrostatic or osmotic pressure difference across the semipermeable wall. The polymers are known to the art in U.S. Pat. Nos. 3,845,770; 3,916,899; and 4,160,020; and in *Handbook of Common Polymers* by Scott, JR and Roff, WJ, 1971 published by CRC Press, Cleveland, Ohio.

In drawing FIG. 2, dosage form 10 in compartment 14 comprises anti-Alzheimer's disease drug tacrine 15, which tacrine 15 is present as a member selected from the group consisting of tacrine base, pharmaceutically acceptable organic salt, pharmaceutically acceptable to inorganic salt, including the hydrochloride, hydrobromide, sulfate, phosphate, lactate, citrate, tartrate, malate, maleate, fumarate, ascorbate, gluconate, asparate, salicylate, edisylate, laurate, palmitate, nitrate, borate, acetate, and oleate. The amount of tacrine 15 in dosage form 10 is 10ng to 1200 mg that is delivered over an extended period of up to 30 hours. Tacrine 15 is present in dosage form 10 in individual doses of 25, 40, 60, 80, 100, 150, 250, 300, 400, 650, 750, 1000, and 1200 mg dose of tacrine. Internal compartment comprises additionally tacrine means 16 to effect the delivery of tacrine 15. The means 16 are provided by the invention because tacrine 15 has a low osmotic pressure of 10 atmospheres which leads against incorporating it in and dispensing tacrine from an osmotic form, since, the osmotic pressure of the environment of the gastrointestinal tract is in excess of 10 atmospheres. This appears to lead away from dispensing tacrine 15 from an osmotic dosage form 10. This invention unexpectedly found that tacrine 15 can be delivered from osmotic dosage form 10 by formulating a composition that is a tacrine, drug core, which tacrine 15 core generates an osmotic pressure greater than 10 atmospheres inside dosage form 10 characterized by an osmotic pressure needed for the controlled delivery of tacrine. The drug tacrine 15 has a low osmotic pressure of 10 atmosphere and it requires means 16 for generating an osmotic pressure inside dosage form 10 much greater than the osmotic pressure of the environment of the gastrointestinal tract. The osmotic pressure of the gastrointestinal tract artificial gastric fluid is about 11 atmospheres and as the artificial intestinal fluid is about 9 atmosphere. The low osmotic pressure of tacrine inside the dosage form is insufficient to deliver tacrine unaided from the dosage form at a controlled rate independent of the higher and constantly changing osmotic pressure of the gastrointestinal tract. The physiology of the gastrointestinal tract includes the temporary storage of ingested food as it is reduced to a semiliquid state, the secretion of chemicals and enzymes to assist in ingestion, and contractions of different durations all influence the unpredictability of the osmostic pressure of the gastrointestinal tract. The presence of means 16 generates an osmotic pressure higher than the gastrointestinal environment and it can be determined by using an osmometer such as a Model 320B, Vapor Pressure Osmometer from the Hewlett-Packard Co., Avondale, Pa. The osmotic pressure $\pi$, is expressed in atmospheres, atm. The osmotic pressure is measured in a commercially available osmometer that measures the vapor pressure difference between water and the solution to be analyzed and, according to standard thermodynamic principles, the vapor pressure ratio is converted into osmotic pressure. Another osmometer that can be used for this purpose is the Model 1001-A Knauer Vapor Pressure Osmometer from Utopia Instrumenting, Joliet, Ill. The osmotic pressure is measured as one of the colligative properties of a solution and calibrated in a recorder so that the output, 1 mVFS, directly gives the osmolality value, 1 osmole/kg water FS, according to thermodynamic principles. The values are converted into osmotic pressure. Representative of means 16 are nontoxic compounds that generate an osmotic pressure of 10 atm, or greater. Representative of means 16 comprises a member selected from the group consisting of inorganic salt, organic salt, monosaccharide, disaccharide, pentose, hexose, inorganic acid, organic acid, oxide, esters, alcohol, amines, and imides, as further depicted by sodium phosphate monobasic of 28 atm, sodium phosphate dibasic 29 atm, sodium phosphate dibasic 31 atm, sodium phosphate dibasic 31 atm, sodium phosphate tribasic 36 atm, potassium sulfate 39 atm, dextrose 82 atm, glucose 83 atm, sucrose 85 atm, mannitol succrose combination 170 atm, dextrose succrose combination 190 atm, mannitol dextrose combination 225 atm, lactose dextrose combination 225 atm, potassium chloride 245 atm, lactose sucrose 250 atm, fructose 355 atm, sodium chloride 356 atm, mannitol fructose 415 atm, sucrose fructose combination 430 atm, dextrose fructose combination 450 atm, and lactose fructose combination 500 atm, and further means 16 embraces magnesium sulfate, magnesium chloride, lithium sulfate, potassium acid phosphate, inositol, magnesium succinate, tartaric acid, raffinose, and sorbitol. The amount of osmotic pressure generating means 16 present in the tacrine core is 2 wt % to 60 wt %.

The tacrine core comprises optionally 0.25 wt % to 15 wt % of a binding agent 17 including poly (vinylpyrrolidone) of 10,000 to molecular weight; 0.01 wt % to 10 wt % of a lubricant 18 such as stearic acid, magnesium stearate, magnesium oleate, calcium oleate, oleic acid, potassium palmate and caprylic acid; and a suspending agent 19 consisting of 0 wt % to 20 wt % of a cellulose ether selected from the group consisting of hydroxyalkylcellulose, hydroxypropylcellulose, hydroxymethylcellulose, hydroxyethylcellulose, hydroxypropylmethylcellulose, hydroxypropylethyl-cellulose, hydroxypropylisopropylcellulose, hydroxypropylbutylcellulose, hydroxypropylpentylcellulose, and hydroxypropylhexylcellulose possessing a 9,000 to 350,000 molecular weight. The weight of all components in the tacrine core is equal to 100 wt %.

Figure 3:
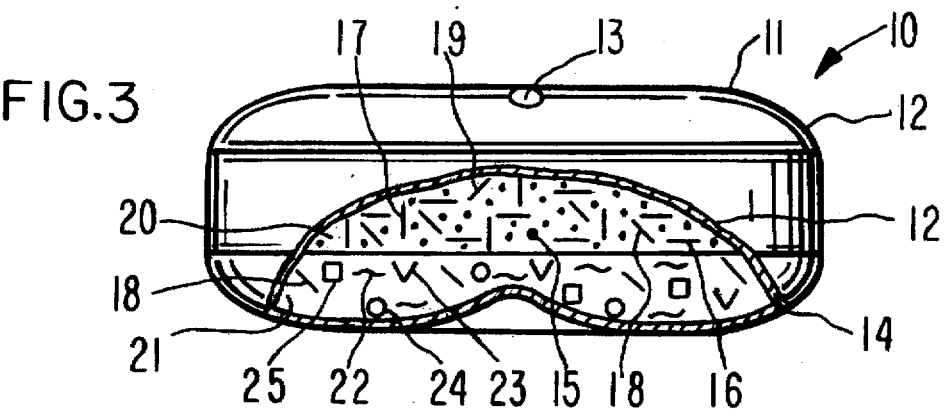
FIG. 3 is an opened view of drawing FIG. 1 illustrating the dosage form comprising a pharmaceutical composition comprising tacrine and displacement means for pushing the pharmaceutical composition containing the tacrine from the dosage form.

In drawing FIG. 3, dosage form 10 is seen in opened section. Dosage form 10 comprises a body 11, a semipermeable wall 12 that surrounds and defines an internal compartment 14. Internal compartment 14 communicates through exit port 13 with the exterior of dosage form 10. Tacrine 15 is present in a core-layer 20 and layer 20 comprises tacrine 15, osmotic means 16 for generating osmotic pressure in compartment 14, a binding agent 17, a lubricant 18, and a suspending agent 19. Compartment 14 comprises a displacement layer 21. Displacement layer 21 is a push layer that cooperates with tacrine-core layer 20 to successfully deliver tacrine 15 from dosage form 10. Displacement layer 21 comprises 40 wt % to 99 wt % of a poly (alkylene oxide) 22 comprising a 3,000 to 7,500,000 molecular weight such as poly(ethylene oxide), poly (propylene oxide), poly(butylene oxide), poly(pentylene oxide), and poly(isopropylene oxide); 0 wt % to 15 wt % of a microcrystalline cellulose 23 possessing a 10,000 to 50,000 molecular weight; 0 wt % to 20 wt % of a hydroxyalkylcellulose 24 possessing a 9,200 to 275,000 molecular weight; 0.5 wt % to 40 wt % of a fluid imbibing compound 25 comprising a member selected from the group consisting of an inorganic salt, organic salt, acid, ester, carbohydrate, oxide, magnesium sulfate, magnesium chloride, sodium chloride, lithium chloride, potassium chloride, potassium sulfate, sodium sulfate, sodium sulfite, lithium sulfate, potassium lactate, mannitol, urea, magnesium succinate, tartaric acid, citric acid, lactic acid, raffinose, sorbitol, sucrose, fructose and glucose; 0 wt % to 3 wt % of a lubricant 18; with the total weight percent, wt %, of all components in displacement layer 21 equal to 100 wt %.

Figure 4:
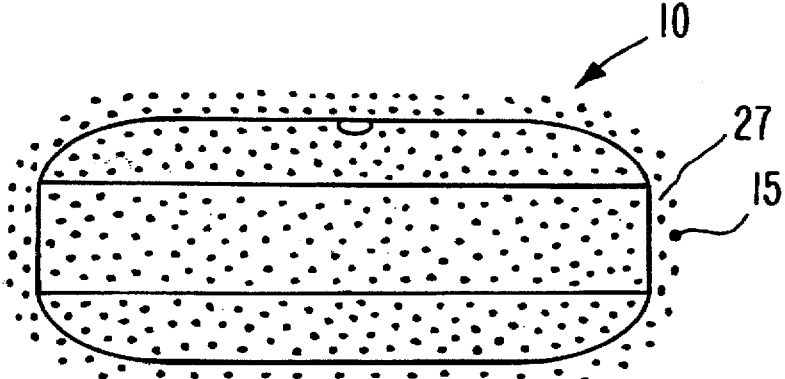
FIG. 4 is a view of the dosage form of drawing FIG. 1 that depicts a coat on the exterior surface of the dosage form which coat comprises tacrine and provides instant-delivery of tacrine.

Dosage form 10, as seen in drawing FIG. 4, illustrates another manufacture provided by this invention. Dosage form 10 comprises an external coat 27 on the exterior surface of dosage form 10. Coat 27 is a therapeutic composition administered from the exterior surface and the therapeutic composition comprises 1 mg to 750 mg of a member selected from tacrine 15 and its pharmaceutically acceptable salts. Therapeutic composition 27 comprises tacrine blended with an aqueous tacrine carrier, which term aqueous releasable includes biological fluid releasable carrier. The carrier comprises 1 mg to 750 mg of a member selected from the group consisting of alkyl cellulose, hydroxyalkylcellulose, hydroxyporpylalkylcellulose, pectin, locus bean gum, gum tragacanth, guar gum, carrageenan, acacia, alginate, xanthan gum, and agar possessing a 5,000 to 1,000,000 molecular weight. Therapeutic composition 27 in another manufacture can comprises 0.25 mg to 17.5 mg of polyethylene glycol. Further, therapeutic composition 27 can comprise 0.25 mg to 17.5 mg of acetylated triglyceride. Therapeutic composition 27 provides a dose amount of tacrine 16 as composition 27 dissolves or undergoes dissolution in the gastrointestinal tract in the presence of gastrointestinal fluid to a tacrine receiving patient. Coat 27 provides immediate tacrine, and up to 1 hour of tacrine on entrance into the gastrointestinal tract for immediate tacrine 15 fluid.

Figure 5:
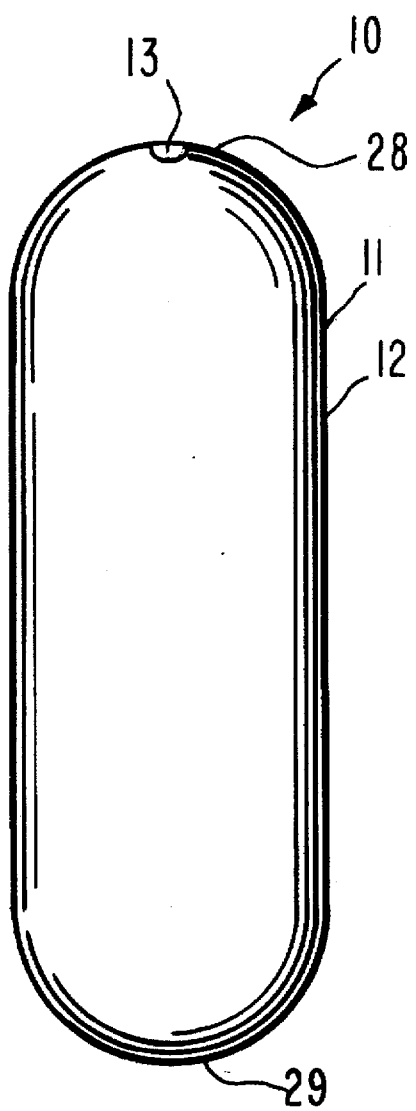
FIG. 5 illustrates the dosage form manufactured as a caplet comprising a continuous body with a pair of curved-rounded ends for increasing the dose of tacrine delivered and for increasing the swallowability of the dosage form caplet.

Drawing FIG. 5 illustrates dosage form 10 designed as a caplet. In drawing FIG. 5, dosage form caplet 10 comprises a body 11, a wall 12, an exit passageway 13, a lead end 28 and a t railing or rear end 29.

Figure 6:
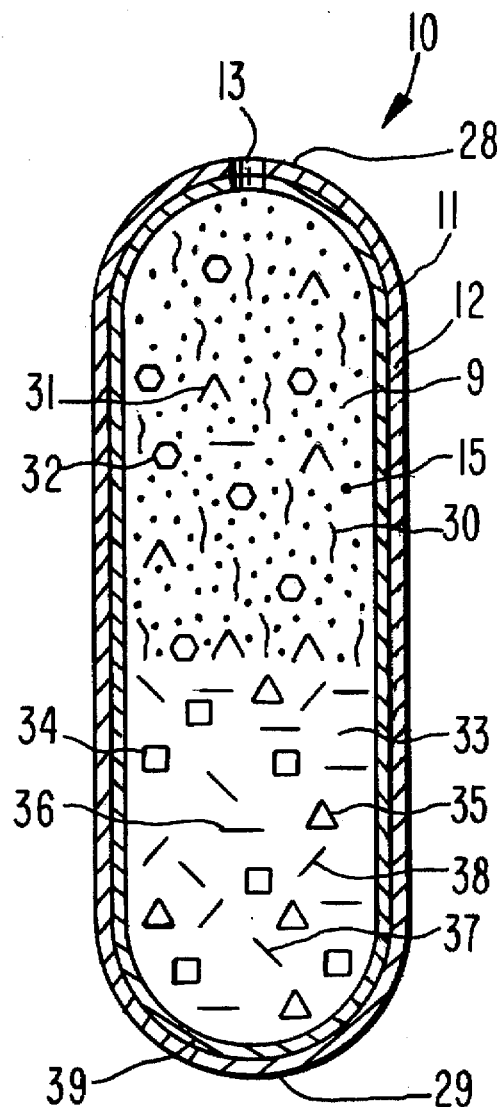
FIG. 6 illustrates the dosage form caplet of drawing FIG. 5 in opened section provided with an outer semipermeable wall and an inner gelatin wall with the caplet comprising tacrine and means for delivering tacrine from the dosage form.

Drawing FIG. 6 illustrates dosage form 10 of drawing FIG. 5 in opened section. In drawing FIG. 6, dosage form 10 comprises a caplet shape adapted and sized for oral admittance into the gastrointestinal tract of a human. The dosage form caplet is illustrated in an oblong-shape for delivering the maximum dose of tacrine 15. The dosage form caplet 10 comprises a vertical-caplet shape, of cylindrical geometry, to effect substantially 100% of tacrine from dosage caplet 10. Dosage caplet 10 comprises a single unit body 11 comprising lead end 28 and a rear end 29, that in one embodiment are round or oval shaped to increase delivery of tacrine 15. Dosage form 10 comprises a semipermeable wall 12 that surrounds an internal compartment 14. Semipermeable wall 12 is permeable to the passage of a fluid, an aqueous or biological fluid present in an environment of use, such as an animal including a human. The semipermeable wall 12 is nontoxic, substantially inert and it maintains its physical and chemical integrity during the tacrine dispensing life of dosage caplet 10.

Compartment 14 comprises a tacrine composition present as a tacrine composition layer 9 that comprises 100 ng to 1500 mg of tacrine 16, or tacrine pharmaceutically acceptable salt, 25 mg to 450 mg of a member 30 selected from the group consisting of carboxymethylcellulose, potassium carboxymethylcellulose and sodium carboxymethylcellulose having a 50,000 to 750,000 molecular weight, 15 mg to 120 mg of a polyol 31 of the formula $(CH_2OH)(CHOH)_n(CH^2OH)$ wherein n is 2 to 5 as represented by sorbitol, mannitol and malititol, 5 mg to 30 mg of a binding agent 32 selected from the group consisting of poly(vinyl pyrrolidone), poly(vinyl carbazole), poly(vinyl pyridine), poly(vinyl oxazole), poly(vinyl methyloxozolidone), poly (vinyl formyl), copolymer of polyvinylpyrrolidone with vinyl acetate, copolymer of polyvinylpyrrolidone and vinyl alcohol, copolymer of polyvinylpyrrolidone with vinyl chloride, copolymer of polyvinylpyrrolidone with vinyl fluoride, copolymer of polyvinylpyrrolidone with vinyl butyrate, copolymer of polyvinylpyrrolidone with vinyl laurate, and copolymer of polyvinylpyrrolidone with vinyl stearate, and poly(vinyl butyrol) of 1000 to 1,000,000 molecular weight, and 0.025 mg to 5 mg of a lubricant selected from group consisting of calcium stearate, magnesium stearate, sodium stearate, potassium stearate, stearic acid, potassium oleate, potassium laurate, and sodium linoleicate. A dye can be present in compartment 14 for aiding in identifying tacrine 16 present in osmotic caplet 10.

Osmotic dosage caplet 10 comprises a displacement or expandable driving layer 33 that imbibes fluid and increases in volume thereby operating to push the tacrine composition through exit passageway 13 from dosage caplet 10. Displacement layer 33 comprises 30 to 225 mg of a hydrogel 34 selected from the group consisting of carboxymethylcellulose, sodium carboxymethylcellulose, potassium carboxymethylcellulose, sodium carboxyethylcellulose, sodium carboxypropylcellulose, calcium carboxymethylcellulose, potassium carboxyisopropylcellulose, sodium carboxymethylethylcellulose, and sodium carboxymethylhydroxyethylcellulose having a 2,500,000 to 7,500,000 molecular weight, 20 mg to 100 mg of an aqueous imbibing compound 35 selected from salt, monosaccharide, disaccharide, ester, acid, ether, amide, imide, and oxide, 1 mg to 20 mg of a hydroxyalkylcellulose 36 comprising a 9,200 to 50,000 molecular weight, 1 mg to 20 mg of a hydroxypropylalkylcellulose 37 comprising a 9,200 to 75,000 molecular weight, 0.01 mg to 3.0 mg of a lubricant 38, and 0 mg to 2 mg of ferric oxide.

Dosage caplet 10, in a further embodiment comprises an inner coat 39. Coat 39 surrounds the tacrine composition layer and the displacement layer, and coat 39 is positioned between the inside surface of wall 12 and in contact with both inside wall 12 and layer 9 and layer 33. Coat 39 comprises a coat-forming composition selected from the group consisting of 100 wt % gelatin having a viscosity of 10 to 40 centipois and a bloom value of 160 to 250, a coat comprising 60 wt % to 99 wt % gelatin and 1 wt % to 40 wt % of a polysaccharide selected from the group consisting of agar, acacia, karaya, tragacanth, algin and guar; a coat comprising 40 wt % to 80 wt % hydroxy-propylcellulose and 20 wt % to 50 wt % hydroxypropylalkylcellulose represented by hydroxypropylmethylcellulose. The total weight of all components in coat 39 is equal to 100 wt %.

The phrase controlled-release as used herein, indicates that control is exercised over both the duration and the profile of the tacrine-release pattern. The expression passageway, as used for the purpose of this invention, includes aperture, orifice, bore, pore, porous element through which the tacrine can be pumped, diffuse, travel or migrate, a hollow fiber, capillary tube, porous overlay, porous insert, microporous member, and porous composition. The expression also includes a compound that erodes or is leached from wall 12 in the fluid environment of use to produce at least one passageway 13 in dosage form 10. Representative compounds suitable for forming at least one passageway, or a multiplicity of passageways, includes an erodible poly(glycolic) acid or poly(lactic) acid member in the wall; a gelatinous filament; a water-removable poly (vinyl alcohol); leachable compounds such as fluid removable pore-forming polysaccharides, acid, salts, or oxides. A passageway or a plurality of passageways can be formed by leaching a compound such as sorbitol, sucrose, lactose, fructose, or the like, from the wall to provide a controlled-release dimensioned pore-passageway. The passageway can have any shape such as round, triangular, square, elliptical, and the like, for assisting in the controlled-metered release of tacrine from dosage form 10. Dosage form 10 can be constructed with one or more passageways in spaced apart relation to one or more surfaces of a dosage form 10.

Passageway 13 and equipment for forming passageways are disclosed in U.S. Pat. Nos. 3,845,770 and 3,916,899 by Theeuwes and Higuchi; in U.S. Pat. No. 4,063,064 by Saunders et al.; and in U.S. Pat. No. 4,088,864 by Theeuwes et al. Passageways comprising controlled releasing dimension, sized, shaped and adapted as a releasing-pore formed by aqueous leaching to provide a releasing-pore of controlled release-rate are disclosed in U.S. Pat. No. 4,200,098 by Ayer and Theeuwes; and in U.S. Pat. No. 4,285,987 by Ayer and Theeuwes.

Wall 12 is manufactured in one process, comprises an air suspension process. This procedure consists in suspending and tumbling a compressed tacrine core comprising a single layer as seen in the above figures, or a bilayer core, as seen in the above figures, in a current of air and wall forming composition until a wall is applied to the tacrine compartment. The air suspension procedure is well-suited for independently forming the wall. The air suspension procedure is described in U.S. Pat. No. 2,799,241; *J Am Pharm Assoc*, Vol 48, pp 451–454 (1959); and ibid, Vol 49, pp 82–84 (1960). Dosage form 10 can be coated also with a wall-forming composition in a Wurster® air suspension coater, using methylene dichloride-methanol cosolvent, for example, 80:20, wt:wt, an ethanol-water, or acetone-water cosolvent, for example, 95:5 wt:wt using 2.5 to 4% solids. An Aeromatic® air suspension coater using a methylene dichloride-methanol cosolvent for example, 80:20 wt:wt, can be used for applying wall 12. Other wall forming techniques such as a pan-coating system, wherein wall forming compositions are deposited by successive spraying of the composition on the drug-core compartment, accompanied by tumbling in a rotating pan. Finally, the wall coated compartments are dried in a forced air over at 30° C. to 50° C. for up to a week to free dosage form 10 of solvent. Generally, the walls formed by these techniques have a thickness of 1 to 30 mils (0.0254 mm to 0.762 mm).

Dosage form 10 of the invention is manufactured by standard manufacturing techniques. For example, in one manufacture the tacrine and other core-forming ingredients comprising a single drug layer or bilayer tacrine-displacement core facing the exit means 13 are blended and pressed into a solid layer, or a solid bilayer. The tacrine and other ingredients can be dry-blended or blended with a solvent and mixed into a solid or semi-solid formed by convention methods such as ballmilling, calendaring, stirring, roll-milling or churning and then pressed into a preselected shape adopted for use in the gastrointestinal tract. The layer possesses dimensions that correspond to the internal dimensions of the area the layer is to occupy in the dosage form, and in a bilayer dosage form it also possesses dimensions corresponding to the second layer for forming a contacting arrangement therewith. Next, in a bilayer core, the push layer is placed in contact with the tacrine layer. The push layer is manufactured using techniques for providing the tacrine layer. The layering of the tacrine layer and the push layer can be fabricated by convention press-layering techniques. Finally, a single tacrine layer or the two tacrine displacement layer compartment forming members are surrounded with an outer wall. A passageway is laser through the wall. The dosage form is optically-oriented automatically by the laser equipment for forming the passageway on the preselected surface for forming the passageway.

In another manufacture, dosage form 10 is manufactured by the wet granulation technique. In the wet granulation technique, for example, tacrine and the ingredients comprising the tacrine-forming layer are blended using poly (vinylpyrralidine) added to a solvent, such as ethyl alcohol-water 98:2 v:v (volume:volume) as the granulation fluid. Other granulating fluid, such as denatured alcohol 100%, can be used for this purpose. The ingredients forming the tacrine layer are individually passed through a mesh screen, usually 40 mesh, and then thoroughly blended in a mixer. Next, other ingredients comprising the tacrine layer are dissolved in a portion of the granulation fluid, such as the cosolvent described above. Then, the latter prepared wet blend is slowly added to the tacrine blend with continual mixing in the blender. The granulating fluid is added until a wet blend is produced, which wet mass then is forced through a 20 mesh screen onto oven trays. The blend is dried for 18 to 24 hours at 30° C. to 50° C. The dry granules are sized then with usually a 20 mesh screen. Next, a lubricant is passed through a screen, such as an 80-mesh screen, and added to the dry screen granule blend. The granulation is placed in a blender and blended for 1 to 10 minutes. A push layer is made by the same wet granulation techniques. The compositions are compressed into their individual layers as a bilayer core in a Manesty® layer press.

Another manufacturing process that can be used for providing the compartment-forming composition layers comprises blending the powdered ingredients for each layer independently in a fluid bed granulator. After the powders are dry blended in the granulator, a binder fluid, for example poly(vinylpyrrolidone) in water, or denatured alcohol, or in 95:5 ethyl alcohol/water, or blends of ethanol and water, is sprayed on the powders. Optionally, the ingredients can be dissolved or suspended in the granulating fluid. The coated powders are then dried in the fluid-bed granulator. This process granulates all the ingredients present therein while adding the granulating fluid. After the granules are dried, and discharged from the fluid bed granulator a lubricant such as stearic acid or magnesium stearate is added to the granulator. The granules for each separate layer are compressed into bilayer cores in the manner described above.

Dosage for 10 of the invention can be manufactured by mixing tacrine with composition-forming ingredients and pressing the composition into a layer possessing dimensions that correspond to the internal dimensions of the compartment of dosage form 10. In another manufacture the tacrine and other tacrine composition-forming ingredients and a solvent are mixed into a solid, or a semisolid, by conventional methods such as ballmilling, shaking, calendaring, tumbling, stirring or rollmilling, and then pressed into a preselected layer-forming shape. Next, a layer of a composition comprising an expandable hydrogel and an optional fluid imbibing compound are placed in contact with the tacrine layer. The layering of the first layer comprising tacrine and the second layer comprising the hydrogel and the optional fluid imbibing compound can be accomplished by using a conventional layer press technique. the wall can be applied by molding, brushing, spraying or dipping the pressed bilayer's shapes with wall-forming materials. Another technique that can be used for applying the wall is the air-suspension coating procedure. This procedure consists in suspending and tumbling the two contacting layers in a current of air solution spray until the wall-forming composition surrounds the layers. The air suspension procedure is described in U.S. Pat. No. 2,799,241; *J Am Pharm Assoc.*, Vol 48, pp 451–454 (1979); and, ibid, Vol 49, pp 82–84 (1960). Other standard manufacturing procedures are described in *Modern Plastics Encyclopedia*, Vol 46, pp 62–70 (1969); and in *Pharmaceutical Science*, by Remington, 14th Ed, pp 1626–1678 (1970), published by Mack Publishing Co, Easton, Pa.

The present invention manufactures a dosage form caplet 10 by surrounding a pressed solid caplet-shaped solid body 11 with a semipermeable wall 12, or first with a coat 39 followed by semipermeable wall 12. One method of manufacture comprises inserting a pressed body into a caplet channel machine leaving one end exposed that is dipped into wall-forming bath to coat the exposed end, followed by dipping the other uncoated end into the bath to surround the end with a wall-forming composition. In one manufacture, the caplet is coated with a semipermeable wall and then permitted to dry with rotation for spreading evenly the wall-forming semipermeable wall around the body of the caplet. In another manufacture, a subcoat is applied to the body of the caplet. Next, after the caplet is permitted to dry it is followed by coating the body of the caplet in a semipermeable wall-forming bath. Inner coat 39 in this manufacture serves as a lubricating coat to facilitate high drug loading of caplet 10 and to facilitate the uninhibited delivery of tacrine 16 from dosage form caplet 10. That is, by lubricating wall 12 it substantially eliminates resistance of tacrine delivery from caplet 10.

Another manufacture comprises filling a caplet die with the composition to be compressed into a shape corresponding to the die cavity, and then removing the compressed body from the cavity. The die cavity is lubricated prior to filling the cavity to prevent sticking and to make it easy to remove the compressed caplet-shaped body from the die cavity. The die cavity may be lubricated with a lubricant such as stearic acid, magnesium stearate, calcium stearate, sodium lauryl sulfate or potassium lauryl sulfate. Next, the caplet body is surrounded with a wall. A wall can be applied by using standard wall-coating equipment. Equipment that can be used for coating the compressed body include the Accela-Cota® coater, High-Coater® coater or the Wurster® suspension coater. The coaters comprise a vaporizer to facilitate drying, and an exhaust system designed to remove solvent vapors and any possible dust. The coating can be effected by using spray guns, and atomizing equipment to introduce a wall-forming solution into a coating pan, or to introduce a wall-forming solution into an air suspension column. Optionally, cold or warm air can be introduced into the spraying cycle to regulate coating and/or drying of the coated caplet. The coating solution can be applied by using a peristaltic spray pump or a pneumatic displacement pump, in continuous or interrupted spray and dry patterns. The coating composition is sprayed to a preselected desired thickness, usually for each separate wall 0.25 mm to 5 min.

Another manufacture that can be used for coating a pressed caplet body, previously pressed in a plate process, rotary die process, a reciprocating die process, or a continuous rotary press, or high pressure station rotary press, or high pressure station rotary press, in one manufacture comprises placing a caplet-forming film over a lower mold with the caplet forming formulation poured onto the film. Then, a film of a wall-forming composition is placed over the caplet body followed by the top mold. The mold is placed under a press and pressure applied with or without heat to form the caplet. The caplet can be made with a passageway. The passageway is integrally formed by the mold set equipped with a passageway-forming area that presents coating in the passageway area.

Another manufacture of caplet 10, is manufactured by standard granulation techniques. For example, the caplet forming ingredients are formulated by the wet granulation technique using an organic cosolvent, such as isopropyl alcohol-methylene dichloride, 80/20, v/v, (volume/volume) as the granulating fluid. The ingredients forming the caplet comprising tacrine and other caplet forming ingredients are individually passed through a 40 mesh screen and then thoroughly blended in a blender. The screens used herein are U.S. Standard Sieves. Next, a polymer, for example, poly (vinylpyrrolidone) is dissolved in a portion of granulation fluid, in the cosolvent described above. Then, the poly (vinylpyrrolidone) solution is slowly added to the dry powder blend with continual mixing in a blender. The granulation fluid is added until a wet blend is produced, generally about 400 cc of granulating fluid per kilogram of blend. The wet mass blend then is forced through a usually 16 to 30 mesh screen onto trays and dried for 18 to 30 hours at 40° C. to 60° C. The dried granules are sized with a usually 20 mesh screen. Next, a lubricant such as magnesium stearate passed through an 80 mesh screen is added to the dry screened granular blend, and blended for 1 to 5 minutes.

In another process and other caplet-forming compositions are blended in a fluid bed granulation. After the powders are dry blended, a granulation fluid comprising an aqueous granulation fluid is sprayed onto the powders and dried in the granulator. This process granulates all of the ingredients together while adding the granulation solution. After the granules are dried, a lubricant such as magnesium stearate is added to the granulation. The caplet forming blend, in either of the above processes, is then pressed into a caplet using a tablet press. The speed of the press is set optionally at 30 rpm and the maximum load set at 0.5 to 20 tons. Then, the caplet body is surrounded with a wall. The dosage form caplet, in another manufacture, is made by mixing tacrine with fluid imbibing compound and/or a hydrogel, and pressed into a solid possessing dimensions that corresponds to the internal dimensions of the caplet; or tacrine and other caplet formulation forming ingredients and a solvent are mixed by conventional methods such as ballmilling, calendaring, stirring or rollmilling, and then pressed into a preselected shape. Next, a layer of a composition comprising a fluid imbibing compound, and/or a hydrogel is placed in contact with a layer of tacrine formulation, and then the two contacting layers, except for a caplet mouth, are surrounded with a semipermeable wall. The wall can be applied by protecting the caplet orifice to keep it open free from coating with a semipermeable wall-forming material. The wall can be applied by molding, spraying, or dipping the pressed shapes into wall-forming materials. Another and presently preferred technique that can be used for applying the wall is the air suspension coating procedure. This procedure consists in suspending and tumbling the pressed compositions in a current of air and a wall forming composition until the wall surrounds the two pressed compositions. The air suspension procedure is described in U.S. Pat. No. 2,799,241; *J Am Pharm Assoc,* Vol 48, pp 451–59 (1979); and, ibid, Vol 49, pp 82–84 (1960). Other standard manufacturing procedures are described in *Modern Plastics Encyclopedia,* Vol 46, pp 62–70 (1969); and in *Pharmaceutical Science,* by Remington 14th Ed, pp 1626–1978 (1970), published by Mack Publishing Co., Easton, Pa.

Exemplary solvents suitable for manufacturing include inert inorganic and organic solvents that do not adversely harm the materials and the final dosage form. The solvents broadly include members selected from the group consisting of aqueous solvents, alcohols, ketones, esters, ethers, aliphatic hydrocarbons, halogenated solvents, cycloaliphatic hydrocarbons, halogenated solvents, cycloaliphatics, aromatics, heterocyclic solvents, and mixtures thereof. Typical solvents include acetone, diacetone, alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclooctane, benzene, toluene, naptha, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE OF EXAMPLES OF THE INVENTION

The following examples are merely illustrative of the present invention and they should not be considered as limiting the scope of the invention in any way as these examples and other equivalents thereof will become apparent to those versed in the art in the light of the present disclosure, the drawings and accompanying claims.

EXAMPLE 1

A dosage form is manufactured for dispensing oral tacrine to the gastrointestinal tract of a patient. It is unexpected to provide a dosage form for dispensing tacrine to the gastrointestinal tract as tacrine has a low osmotic pressure of about 10 atmospheres that is substantially equivalent to the actual osmotic pressure of 8 plus atmospheres of the gastrointestinal tract. The osmotic pressure of the gastrointestinal tract is unpredictable and variable. Thus, a dosage form provided by this invention must develop an internal osmotic pressure greater than the osmotic pressure of the gastrointestinal tract, for this invention at least 30 atmospheres in the dosage form, to provide a controlled rate of delivery of tacrine over a prolonged time. This invention effects an internal osmotic pressure of at least 30 atmospheres by blending tacrine, for example tacrine hydrochloride, with a fluid imbibing compound possessing an osmotic pressure gradient across a semipermeable wall of 20 atmospheres or more, for example mannitol, to provide a combined tacrine hydrochloride fluid imbibing composition of 30 atmospheres. The mutual solubilities of tacrine hydrochloride and fluid imbibing mannitol, which has an osmotic pressure of 40 atmospheres, exhibited an osmotic pressure of 58 atmospheres. The mutual solubilities of tacrine-fluid imbibing osmotic pressure generating compound in water at 37° C. at saturation, are in one embodiment in a ratio of 1:1 by weight, or a molar ratio of 0.72:1. The invention prepares an osmotic core formulation by combining tacrine, presently tacrine hydrochloride monohydrate, with the osmotic pressure generating compound mannitol in a 1:1 ratio by weight to produce a homogenous blend. The blend is converted into a wet granulation by wetting the blend with a binding composition comprising poly(vinyl-pyrrolidone) and ethanol. the fresh mass is passed through a screen, 20 mesh, and oven dried at 50° C. overnight. Next, the dry granules are passed through a 20 mesh screen and a lubricant, magnesium stearate, is added to the dry granules and blended for 5 minutes. The composition is compressed into a single layer tacrine cores to provide the separate core formulations: (1) a core comprising 86.15 mg of tacrine hydro-chloride, 86.15 mg of mannitol, 7.25 mg of poly(vinylpyrrolidone), and 1.81 mg of magnesium stearate, and (2) a core comprising 65.24 mg of tacrine hydro-chloride monohydrate, 65.24 mg of mannitol, 3.47 mg of poly(vinyl-pyrrolidone), 0.69 mg of hydroxypropylmethylcellulose and 4.16 mg of magnesium stearate.

Next, a semipermeable wall is coated around the individual, separate cores. The semipermeable wall forming composition comprises 80 wt % cellulose acetate having a 39.8% acetyl content and 20 wt % poly (vinylpyrrolidone). The cores are coated in a 305 mm pan. The final semipermeable wall coated cores are dried for 18 hours at 45° C. in a light current of air. An exit passageway is drilled through the semipermeable wall connecting the tacrine with the exterior of each dosage form. The exit port has a diameter of 30 mils (0.76 mm) and each dosage form dispenses tacrine for 24 hours.

EXAMPLE 2

A dosage form adapted, designed and shaped as an osmotic tacrine dosage form is manufactured as follows: first, 3,290 g of tacrine hydrochloride and 3,290 g of mannitol are added to a Freund Flow-Coater® bowl, a fluid bed granulator. The bowl is attached and the granulation process is initiated. Next, the dry materials are air suspended and mixed for 7 to 8 minutes. Then, a solution prepared by dissolving 175 g of poly (vinylpyrrolidone) having a molecular weight of 40,000 in 260 g of distilled water is sprayed onto the materials. The coating conditions are monitored during the process of spraying the aqueous poly (vinylpyrrolidone) at a solution spray rate of 125 g/min with an inlet temperature of 45° C. and an air flow of 1000 cfm. Next, the coated granules are blended with 35 g of hydroxypropylmethylcellulose and 210 mg of magnesium stearate and the granulation transferred to a Rotocone® and mixed to provide homogenous granules.

Next, a hydrogel expansion composition is prepared as follows: first, 950 g of pharmaceutically acceptable poly (ethylene oxide) comprising a 5,000,000 molecular weight, 35 g of microcrystalline cellulose, 25 g sodium chloride, 5.15 g hydroxypropylcellulose of 50,000 molecular weight, 5.15 g of hydroxypropylmethyl-cellulose of 11,200 molecular weight, and, 1.44 g of ferric oxide, with all the ingredients separately screened through a 40 mesh screen. Then, all the materials are transferred to a mixer and mixed for 5 minutes. Then, 400 ml of denatured ethyl alcohol is added to the mixed powders in the mixer and the mixing continued for 3 minutes. The homogenous mixed mass is passed through a 16 mesh screen and allowed to dry at room temperature for 16 hours and then rescreened through a 20 mesh screen. The screened granulation is mixed with 2.5 g magnesium stearate in a roller mill for 6 minutes.

Next, the tacrine composition and the hydrogel composition are compressed into a bilayer core. First, 420 mg of the tacrine composition is added as a first layer to a punch and tamped, then 215 mg of the hydrogel composition is added as a second layer to the punch. The layers are compressed under a compression force of two tons into contacting layered arrangement.

Then, the bilayered cores are coated with a semipermeable wall. The wall forming composition comprises 60 wt % cellulose acetate having a 39.8% acetyl content, 25 wt % hydroxypropylcellulose having a 18,500 molecular weight, and 15 wt % polyethylene glycol 3350. The wall-forming composition is dissolved in an acetone: methanol (80:20 wt:wt) cosolvents to make 4.5% solids solution. The wall forming composition is sprayed onto and around the bilayer cores in a 24" (60 cm) Vector® Hi-Coater.

Next, two 25 mil (0.635 mm) exit passageways are drilled through the semipermeable wall to connect the tacrine layer with the exterior of the dosage form. The residual solvent is removed by drying for 48 hours at 50° C. and 50% humidity. Next, the dosage forms are dried a minimum of 4 hours at 50° C. to remove excess moisture. The dosage form, on oral admittance into the gastrointestinal tract provides tacrine to an Alzheimer patient.

The dosage form provided by this invention is unexpected as tacrine experimentally exhibits a low osmotic pressure. The solubility of tacrine at 37° C. in water is 212 mg/ml with an osmotic pressure of 10 atmospheres, the solubility of tacrine in artificial gastric fluid is 168 mg/ml with an osmotic pressure of 19 atmospheres and the solubility of tacrine in artificial intestinal fluid is 205 mg/ml with an osmotic pressure of 18 atmosphere. These data lead-away from providing a dosage form comprising tacrine because of the much higher osmotic pressure of the environment of gastrointestinal tract, combined with the unknown and variable osmotic pressure of the gastrointestinal tract, often resulting from fluid fluctuation, digestion and absorption in the gastrointestinal tract. This invention enhances tacrine osmotic pressure by augmenting tacrine's osmotic pressure by 20 atmospheres to effect the delivery at a controlled rate of tacrine from the dosage form.

EXAMPLE 3

An osmotic dosage form possessing a vertical length greater than its cross-section is manufactured for delivering substantially 100% of its tacrine. The osmotic dosage form comprises a caplet shape, of cylindrical geometry. The osmotic caplet comprises an internal coat to improve the structure and the performance of the osmotic caplet and provide tacrine in a controlled programmable rate. An osmotic caplet is manufactured by blending 9.0 g of tacrine hydrochloride monohydrate, 12.9 g sodium carboxymethyl cellulose of 90,000 molecular weight, and 6.60 g of sorbitol are blended in a roll mill for 15 minutes. Next, 1.20 g of poly(vinylpyrrolidone) of 35,000 molecular weight dissolved in 10 ml of ethyl alcohol is added to the blend and granulation continued for 5 to 8 minutes. The wet granulation is screened through a 20 mesh screen and dried over night for 18 hours at 25° C. Then, 0.30 g of magnesium stearate is added to the dry granules and blended for an additional 5 minutes.

Next, the osmotic granulation, a displacement composition is prepared by blending 4,112.5 g of sodium carboxymethylcellulose of 700,000 molecular weight, 2,100.0 g of sodium chloride, 350.0 g of hydroxypropylcellulose of 60,000 molecular weight in a fluid bed granulator, and all the ingredients blended for 5 to 10 minutes. Then, a granulation fluid comprising 350.0 g of hydroxypropylmethylcellulose of 11,200 molecular weight as a 5% aqueous solution is added to the fluid bed. The granulation fluid is added slowly by spraying it onto the fluidizing bed. Fluidization is continued for an additional 15 minutes. Next, the granules are passed through a 16 mesh screen.

Next, a number of solid caplets are prepared by pressing tacrine compositions comprising 108.00 mg of tacrine hydrochloride monohydrate, 154.80 mg of sodium carboxymethylcellulose, 79.20 mg of sorbitol, 14.40 mg of poly(vinylpyrrolidone) and 3.60 mg of magnesium stearate, against a displacement composition comprising 84.60 mg of sodium carboxymethylcellulose, 43.20 mg of sodium chloride, 7.20 mg of hydroxypropylcellulose, 7.20 mg of hydroxypropylmethylcellulose, and 0.36 mg of magnesium stearate compositions. Then, they are added separately to the cavity of a caplet mold and the two compositions compressed into two layer core that is coated with a subcoat composition comprising 70:30 hydroxypropylcellulose having a 80,000 molecular weight and hydroxypropylcellulose 603 having a 9,600 molecular weight applied as an 8% solid aqueous solution. The coat is applied using a 12 inch (30 cm) pan coater. Next, a semipermeable membrane comprising 88:12 (wt:wt) mixture of cellulose acetate comprising a 39.8% acetyl content and polyethylene glycol 4000 molecular weight dissolved in 80/20 acetone methanol as 4% solid solution is coated as a semipermeable wall over the subcoat. The average semipermeable wall applied is 40.3 mg. Next, a 40 mil (1.01 mm) orifice is drilled through the tacrine end of the semipermeable wall and the internal subcoat for delivering tacrine from the caplet. The caplet prepared by this example comprises in the tacrine layer a tacrine composition comprising 108.00 mg tacrine hydrochloride monohydrate, 154.80 mg of sodium carboxymethylcellulose 7LF of 90,000 molecular weight, 79.20 mg of sorbitol, 14.40 mg of poly(vinylpyrrolidone) and 3.60 mg of magnesium stearate; the osmotic layer, a displacement composition comprises 84.60 mg of sodium carboxymethylcellulose, 7HF, 700,000 molecular weight 43.20 mg of sodium chloride, 7.20 mg of hydroxypropylcellulose, 7.20 mg of hydroxy-propylmethylcellulose and 0.36 mg of magnesium stearate; the subcoat comprises 8.26 mg of hydroxypropylcellulose and 3.54 mg of hydroxypropyl-methylcellulose; and the semipermeable wall comprises 32.24 mg of cellulose acetate with a 39.8% acetyl content and 8.06 mg of polyethylene glycol having a 4000 molecular weight. The dosage caplet has a mean release rate of 10.37 mg/hr over 24 hours.

EXAMPLE 4

The procedure of Example 3 is followed in this example, with the manufacturing conditions as described, except that in this example the tacrine composition comprises poly (ethylene oxide) having a 200,000 molecular weight as a replacement for the sodium carboxymethylcellulose, and the displacement layer comprises poly(ethylene oxide) having a 5,000,000 molecular weight that replaces the sodium carboxymethylcellulose.

EXAMPLE 5

The procedure of Example 3 is followed in this example, with the manufacturing steps as set forth, except that in this example the tacrine composition comprises poly(ethylene oxide) of 300,000 molecular weight and the displacement composition comprises poly(ethylene oxide) of 7,800,000 molecular weight.

EXAMPLE 6

This invention pertains further to the use of an easy to administer dosage form for delivering tacrine to the gastrointestinal tract of a patient in need of tacrine therapy. The use of the dosage form comprises: (1) admitting an osmotic caplet orally into the patient; the osmotic caplet comprising (a) a vertical body; (b) a composition comprising 100 ng to 1500 mg of tacrine in the caplet; (c) a displacement composition for imbibing fluid to increase in volume and push the composition comprising the tacrine from the dosage form; (d) a subcoat comprising a hydrophilic composition around the tacrine composition and the displacement composition; (e) a semipermeable wall that surrounds the coat; (f) a curved lead end comprising a passageway for delivering substantially all the tacrine to the patient; (2) imbibing fluid through the semipermeable wall into the caplet; thereby; (3) delivering tacrine to the patient to provide the needed therapy over a prolonged period of time up to 24 hours.

The use of the dosage form for administering tacrine pertains additionally to the dosage form comprising a tacrine core and to the dosage form comprising a bilayer tacrine displacement core. The invention further embraces a method of administering 10 ng to 1200 mg of tacrine selected from tacrine and its pharmaceutically acceptable salts to a patient, wherein the method comprises orally administering to the patient 10 ng to 1200 mg of tacrine and its pharmaceutically acceptable salts at a controlled rate of 0.40 ng/hr to 50 mg/hr from an orally administrable dosage form over an extended period up to 24 hours to administer 10 ng to 1200 mg of tacrine and its pharmaceutically acceptable salts to the patients.

In summary, it will be appreciated the present invention contributes to the tacrine dispensing art by providing an unexpected and unique dosage form that possesses a practical utility, and can administer tacrine at a metered release rate up to 24 hours for preselected tacrine therapy. While the invention has been described and pointed out in detail with reference to operative embodiments thereof, it will be understood by those skilled in the art that various changes, modifications, substitutions and omissions can be made without departing from the spirit of the invention. It is intended therefore, that the invention embraces those equivalents within the scope of the claims which follow.

What is claimed is:

1. An osmotic dosage form for delivering tacrine to the gastrointestinal tract of an Alzheimer's patient, wherein the osmotic dosage form comprises:
    (a) a tacrine composition comprising 86.15 mg of tacrine hydrochloride, 86.15 mg of mannitol, 7.25 mg of poly(vinylpyrrolidone) and 1.81 mg of magnesium stearate;
    (b) a semipermeable wall coated around the tacrine composition, comprising 80 wt % cellulose acetate and 20 wt % poly(vinylpyrrolidone), and,
    (c) an exit passageway in the wall that connects the tacrine composition with the exterior of the dosage form for delivering tacrine over 24 hours.

2. The osmotic dosage form for delivering tacrine according to claim 1, wherein a dose of tacrine is coated on the exterior surface of the semipermeable wall.

* * * * *